(12) United States Patent
Furukawa et al.

(10) Patent No.: US 10,168,290 B2
(45) Date of Patent: Jan. 1, 2019

(54) X-RAY FLUORESCENCE SPECTROMETER

(71) Applicant: SHIMADZU CORPORATION, Kyoto-shi, Kyoto (JP)

(72) Inventors: Hiroaki Furukawa, Kyoto (JP); Kanji Kobayashi, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 252 days.

(21) Appl. No.: 14/894,023

(22) PCT Filed: Sep. 20, 2013

(86) PCT No.: PCT/JP2013/075569
§ 371 (c)(1),
(2) Date: Jan. 6, 2016

(87) PCT Pub. No.: WO2014/192173
PCT Pub. Date: Dec. 4, 2014

(65) Prior Publication Data
US 2016/0116424 A1    Apr. 28, 2016

(30) Foreign Application Priority Data
May 27, 2013  (JP) .................................. 2013-110689

(51) Int. Cl.
*G01N 23/00* (2006.01)
*G01N 23/223* (2006.01)

(52) U.S. Cl.
CPC ..... *G01N 23/223* (2013.01); *G01N 2223/076* (2013.01)

(58) Field of Classification Search
CPC ................. G01N 2223/076; G01N 23/223
See application file for complete search history.

(56) References Cited

U.S. PATENT DOCUMENTS

2008/0212736 A1\* 9/2008 Klein ................... G01N 23/223
378/45

FOREIGN PATENT DOCUMENTS

EP    2270479 A2    1/2011
JP    5256803 A     10/1993
(Continued)

OTHER PUBLICATIONS

Written Opinion of the International Searching Authority in PCT/JP2013/075569, dated Jan. 14, 2014 [PCT/ISA/237].
(Continued)

*Primary Examiner* — Dani Fox
(74) *Attorney, Agent, or Firm* — Sughrue Mion, PLLC

(57) ABSTRACT

The present invention has an object to provide an X-ray fluorescence spectrometer capable of preventing a decrease in analysis precision of light elements whose atomic number is less than 23 and making helium gas replacement for the inside of an analysis chamber more efficient. An X-ray fluorescence spectrometer of the present invention includes: an X-ray tube 12 for irradiating a sample S on a sample stage 14 with a primary X-ray, the sample stage 14 having an X-ray passing port 141; a detector 13 for detecting a fluorescent X-ray emitted from the sample S; an analysis chamber 16 having an introduction port 17 for the primary X-ray emitted from the X-ray tube 12 and a detection port 181 for the detector 13, the analysis chamber 16 containing an internal space including an optical path of the primary X-ray from the introduction port 17 to the X-ray passing port 141 and an optical path of the fluorescent X-ray from the X-ray passing port 141 to the detection port 181; first and second introduction pipes 201 and 202 for introducing helium gas supplied from a helium gas cylinder 22 into the analysis chamber 16 through the introduction port 17 and the detection port 181, respectively; and a flow rate control (Continued)

valve 24 for controlling a helium gas flow rate in each of the first and second introduction pipes 201 and 202.

4 Claims, 6 Drawing Sheets

(56) References Cited

FOREIGN PATENT DOCUMENTS

| JP | 2001-349852 A | 12/2001 |
| JP | 2012229973 A | 11/2012 |
| WO | 2005/100963 A1 | 10/2005 |

OTHER PUBLICATIONS

Communication dated Apr. 6, 2016, issued by the European Patent Office in corresponding European Application No. 13885621.6.

\* cited by examiner

X-RAY FLUORESCENCE SPECTROMETER

CROSS REFERENCE TO RELATED APPLICATIONS

This application is a National Stage of International Application No. PCT/JP2013/075569 filed Sep. 20, 2013, claiming priority based on Japanese Patent Application No. 2013-110689, filed May 27, 2013, the contents of all of which are incorporated herein by reference in their entirety.

TECHNICAL FIELD

The present invention relates to an X-ray fluorescence spectrometer which detects the wavelength (energy) and the intensity of a peak of a fluorescent X-ray that is generated from a solid, powder, or liquid sample when the sample is irradiated with an X-ray, and thus performs a qualitative/quantitative analysis of light element components whose atomic number is less than 23 in the sample.

BACKGROUND ART

An X-ray fluorescence spectrometer irradiates a sample in an analysis chamber with a primary X-ray emitted from an X-ray source, detects a fluorescent X-ray emitted from the irradiated sample by means of a detector, measures the wavelength (energy) and the intensity of a peak of the fluorescent X-ray, and thus performs a qualitative/quantitative analysis of element components in the sample. Here, if the atmospheric air exists in an optical path of the primary X-ray from the X-ray source to the sample as well as in an optical path of the fluorescent X-ray from the sample to the detector, the primary X-ray and the fluorescent X-ray are absorbed and attenuated by the atmospheric air. In particular, light elements whose atomic number is less than 23 each generate a fluorescent X-ray with a long wavelength (low energy), and are strongly influenced by such absorption by the atmospheric air. To deal with this, in the case where light elements are contain d in an analysis target, the atmosphere inside the analysis chamber is replaced with helium gas which absorbs less X-ray than the atmospheric air.

The analysis chamber is provided with a gas supply port and a gas outlet, and helium gas is supplied from the gas supply port while the atmospheric air is pushed out from the gas outlet, whereby the atmosphere inside the analysis chamber is replaced with the helium gas. In addition to the gas supply port and the gas outlet, the analysis chamber is provided with opened parts such as an introduction port for the primary X-ray emitted from the X-ray source and a detection port for the detector. Hence, conventionally, in order to prevent gases from flowing in and out through the opened parts, the opened parts are each covered by a thin organic whereby the helium gas replacement work is made more efficient (see Patent Literature 1).

In the above-mentioned conventional method, however, although organic films that absorbs less X-ray are used, the light elements, which each emit a fluorescent X-ray with a longer wavelength (lower energy) by irradiation with the primary X-ray, a e significantly influenced by the X-ray absorption due to the existence of the organic films in the optical path of the primary X-ray and the optical path of the fluorescent X-ray.

CITATION LIST

Patent Literature

[Patent Literature 1] JP 2001-349852 A

SUMMARY OF INVENTION

Technical Problem

The present invention has an object to provide an X-ray fluorescence spectrometer capable of enhancing the analysis precision of light elements whose atomic number is less than 23 and making helium gas replacement for the inside of an analysis chamber more efficient.

Solution to Problem

An X-ray fluorescence spectrometer according to the present invention, which has been made in order to achieve the above-mentioned object, includes:

a) an X-ray source for irradiating a sample with a primary X-ray;

b) a detector for detecting a fluorescent X-ray that is emitted from the sample when the sample is irradiated with the primary X-ray;

c) an analysis chamber having an introduction port for the primary X-ray emitted from the X-ray source and a detection port for the detector, the analysis chamber confining a space including an optical path of the primary X-ray from the introduction port to the sample and an optical path of the fluorescent X-ray from the sample to the detection port;

d) first introduction means for introducing helium gas into the analysis chamber through the introduction port;

e) second introduction means for introducing helium gas into the analysis chamber through the detection port; and f) flow rate control means for controlling a flow rate of the helium gas that is introduced into the analysis chamber by each of the first introduction means and the second introduction means.

In the above-mentioned X-ray fluorescence spectrometer, it is preferable that the flow a control means include: first flow rate control means for controlling the flow rate of the helium gas that is introduced into the analysis chamber by the first introduction means; and second flow rate control means for controlling the flow rate of the helium gas that is introduced into the analysis chamber by the second introduction means. According to such a configuration, the flow rate of the helium gas that is introduced into the analysis chamber through each of the introduction port and the detection port can be adjusted as appropriate, depending on the positions, structures, or other factors relating to the introduction port and the detection port.

Moreover, it is preferable that: the first introduction means include a first introduction pipe having an inlet-side end part connected to a helium gas supply source and an outlet-side end part connected to the introduction port; the second introduction means include a second introduction pipe having an inlet-side end part connected to the helium gas supply source and an outlet-side end part connected to the detection port; and the X-ray fluorescence spectrometer further include atmospheric air introduction means for forcibly introducing an atmospheric air into the analysis chamber from at least one of the first introduction pipe and the second introduction pipe.

According to such a configuration, the time required to replace helium gas in the analysis chamber with the atmospheric air can be reduced. Moreover, helium gas remaining in the introduction port and the detection port can be reliably replaced with the atmospheric air, and hence influences of helium gas when the sample is analyzed under the atmospheric air can be eliminated.

Advantageous Effects of Invention

According to the present invention, the first introduction means and the second introduction means are provided, and helium gas is introduced from the introduction port for the primary X-ray and the detection port for the detector that are opened parts of the analysis chamber. Hence, in the insides of these opened parts where gas replacement is conventionally difficult, the atmosphere can be efficiently replaced with helium gas. Accordingly, the time before the fluorescent X-ray intensity of each light element detected by the detector becomes stable from a helium gas introduction start can be reduced, the analysis time can be reduced, and the analysis processing capability can be enhanced.

Moreover, the helium gas replacement rates of the introduction port for the primary X-ray and the detection port for the detector are enhanced compared with those in conventional cases. Hence, the fluorescent X-ray intensity of each light element detected by the detector increases, and the analysis sensitivity and the analysis precision can be enhanced.

Further, unlike conventional X-ray fluorescence spectrometers, a member that absorbs X-rays does not exist on the optical paths of the primary X-ray and the fluorescent X-ray. Hence, decrease in the intensity of the primary X-ray radiated to the sample and in the intensity of the fluorescent X-ray that is emitted from the sample and is detected by the detector is prevented, and the qualitative/quantitative analysis precision of light element components whose atomic number is less than 23 in the sample is further enhanced.

DESCRIPTION OF EMBODIMENTS

Hereinafter, some specific embodiments of the present invention are described with reference to the drawings.

First Embodiment

Figure 1:
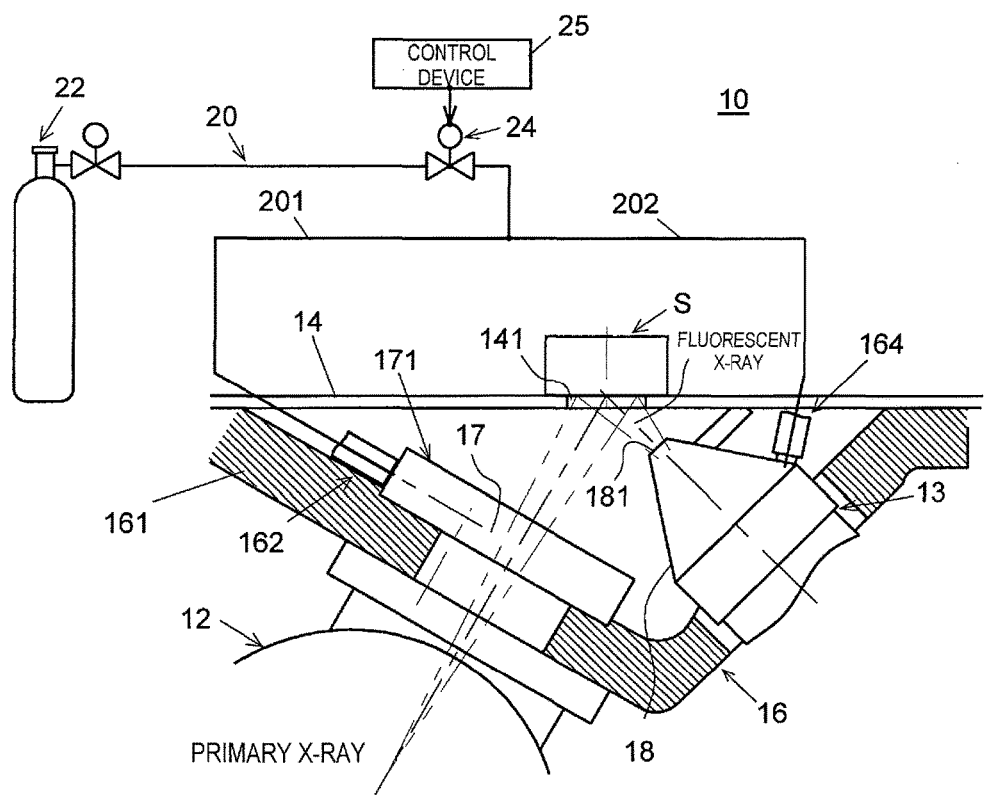
FIG. 1 is a schematic configuration diagram of an X-ray fluorescence spectrometer according to a first embodiment of the present invention.

FIG. 1 is a diagram illustrating a schematic configuration of an X-ray fluorescence spectrometer according to a first embodiment of the present invention. The X-ray fluorescence spectrometer 10 of the present embodiment is an X-ray fluorescence spectrometer of under irradiation type, and includes: an X-ray tube 12 for generating a primary X-ray; a detector 13 (for example, a semiconductor detector, a proportional counter) for detecting a fluorescent X-ray secondary X-ray) generated from a sample; a sample stage 14 having an X-ray passing port 141, and other components.

A lower part of the sample stage 14 is provided with an analysis chamber 16. The analysis chamber 16 is provided with an introduction port 17 for the primary X-ray and a housing 18 to which a leading end part of the detector 13 is attached. The primary X-ray emitted from the X-ray tube 12 enters the analysis chamber 16 from the introduction port 17, passes through the analysis chamber 16, and is radiated to a sample S held by the sample stage 14 through the passing port 141. Moreover, the leading end of the housing 18 is provided with a detection port 181, and the fluorescent X-ray that is emitted from the sample S and comes out from the passing port 141 passes through the analysis chamber 16, and enters the detector 13 through the detection port 181.

The inside of the analysis chamber 16 is in communication with a helium gas cylinder 22 that is a helium gas supply source, through an introduction pipe 20. A flow rate control valve 24 is set to the introduction pipe 20, the degree of opening of the flow rate control valve 24 is adjusted by an instruction from a control device 25, and helium gas is introduced at an appropriate flow rate into the analysis chamber 16.

A guide bush 171 is attached to a lower wall 161 of the analysis chamber 16 near the introduction port 17, and the guide bush 171 is provided with a first gas introduction port 162.

Moreover, the housing 18 is provided with a second gas introduction port 164. The introduction pipe 20 extending from the helium gas cylinder 22 is brandied into two halfway, and leading end parts of the branch pipes 201 and 202 are connected to the first gas introduction port 162 and the second gas introduction port 164, respectively. The branch pipe 201 and the branch pipe 202 correspond to a first introduction pipe and a second introduction pipe of the present invention, respectively. The flow rate control valve 24 is set to the introduction pipe 20 upstream of (on the helium gas cylinder 22 side from) the branch pipes 201 and 202.

In the X-ray fluorescence spectrometer 10 configured as described above, a helium gas replacement rate (He replacement rate) was examined when helium gas was introduced into the analysis chamber 16 while a helium gas flow rate from the introduction pipe 20 was changed. Here, a powder sample of sodium sulfate ($Na_2SO_4$) obtained by press working was used, and the He replacement rate was obtained in the following manner from values (actual measurement values obtained by measuring a Na—Kα, intensity and a S—Kα intensity under this condition.

The fluorescent X-ray intensities of Na—Kα and S—Kα when the atmosphere inside the analysis chamber 16 is replaced with helium gas can be theoretically expressed by the following Expression (1) and Expression (2).

(Na—Kα intensity)=(Na—Kα intensity in vacuum)× (attenuation rate of primary X-ray)×(attenuation rate of Na—Kα)     (1)

(S—Kα intensity)=(S—Kα intensity in vacuum)× (attenuation rate of primary X-ray)×(attenuation rate of S—Kα)     (2)

In Expression (1) and Expression (2), the attenuation rate of the primary X-ray and the attenuation rates of Na—Kα and S—Kα represent the rates of attenuation by helium gas. That is in the case where the atmosphere inside the analysis chamber 16 is completely (100%) replaced with helium gas, theoretically, a value obtained by multiplying the Na—Kα intensity in vacuum by the rates of attenuation of the primary X-ray and Na—Kα by helium gas is an actual measurement value of the Na—Kα intensity, and a value obtained by multiplying the S—Kα intensity in vacuum by the rates of attenuation of the primary X-ray and S—Kα by helium gas is an actual measurement value of the S—Kα intensity.

Because the Na—Kα intensity and the S—Kα intensity in vacuum of a fluorescent X-ray emitted from sodium sulfate, the rates of attenuation of these Na—Kα and S—Kα by helium gas, and the rate of attenuation of the primary X-ray by helium gas are known, the rate (He replacement rate) at which the gas in the chamber 16 is replaced with helium gas can be obtained from the actual measurement values of Na—Kα and S—Kα.

In actuality, because the atmosphere inside the analysis chamber 16 under atmospheric pressure is replaced with helium gas, the actual measurement values of the Na—Kα intensity and the S—Kα intensity are influenced due to absorption of the primary X-ray and the fluorescent X-ray by the atmospheric air in the analysis chamber 16. In view of this, in the present embodiment, a data table showing a relation between: the actual measurement value of Na—Kα and the actual measurement value of S—Kα, and the He replacement rate was created considering attenuation of the prima. X-ray, Na—Kα, and S—Kα by not only helium gas but also the atmospheric air, and the data table was stored in advance in a memory, whereby the He replacement rate was obtained from the actual measurement value of Na—Kα and the actual measurement value of S—Kα.

Figure 2A:
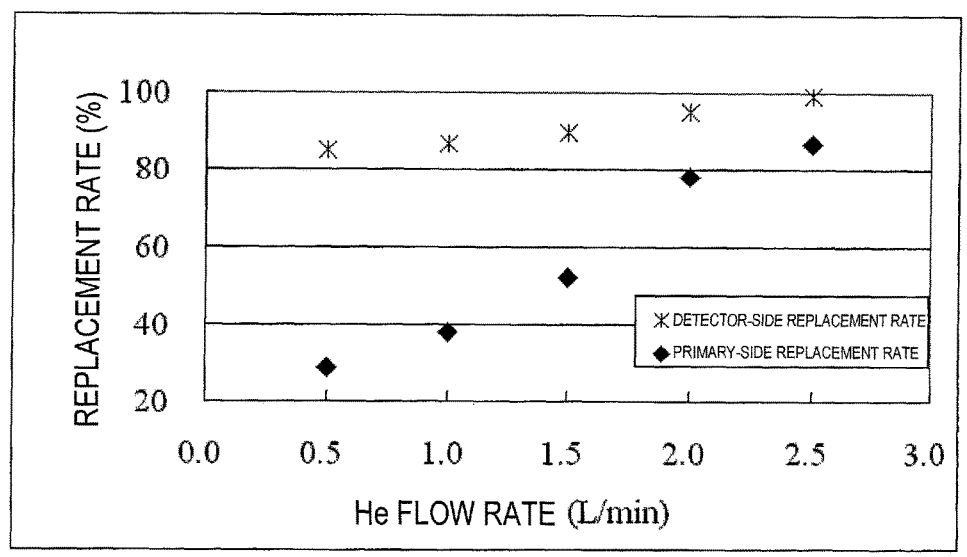
FIG. 2A is a diagram illustrating a relation between a helium gas flow rate and a helium gas replacement rate when helium gas is introduced into a chamber of a conventional X-ray fluorescence spectrometer.
Figure 2B:
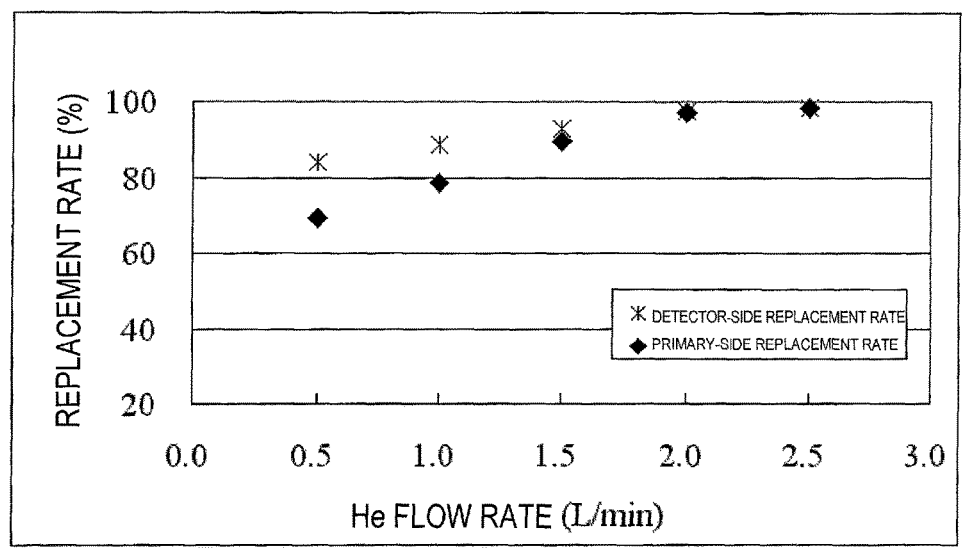
FIG. 2B is a diagram illustrating a relation between a helium gas flow rate and a helium gas replacement rate when helium gas is introduced into a chamber of the X-ray fluorescence spectrometer according to the present embodiment.
Figure 3A:
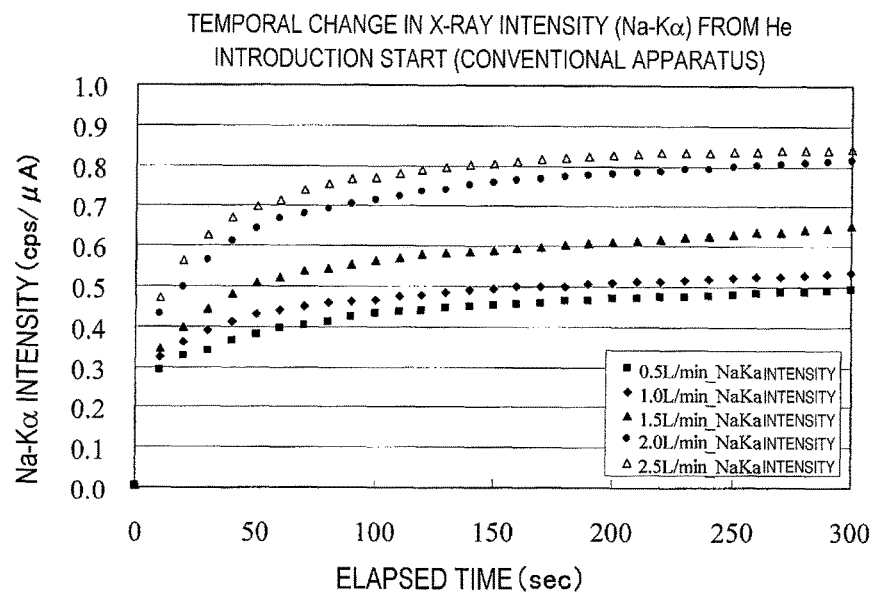
FIG. 3A is a diagram illustrating a temporal change in fluorescent X-ray (Na—Kα) intensity of the conventional X-ray fluorescence spectrometer.
Figure 3B:
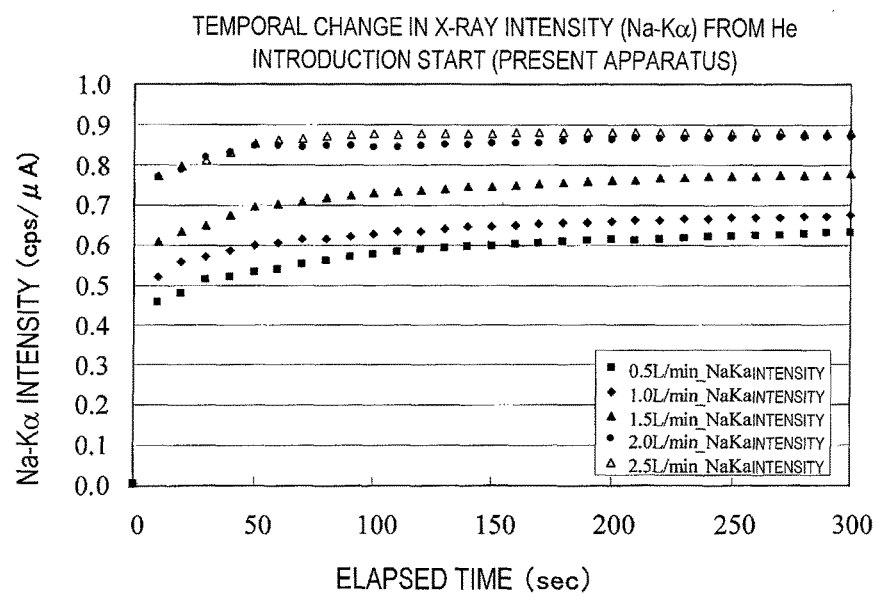
FIG. 3B is a diagram illustrating a temporal change in Na—Kα intensity of the X-ray fluorescence spectrometer according to the present embodiment.
Figure 4A:
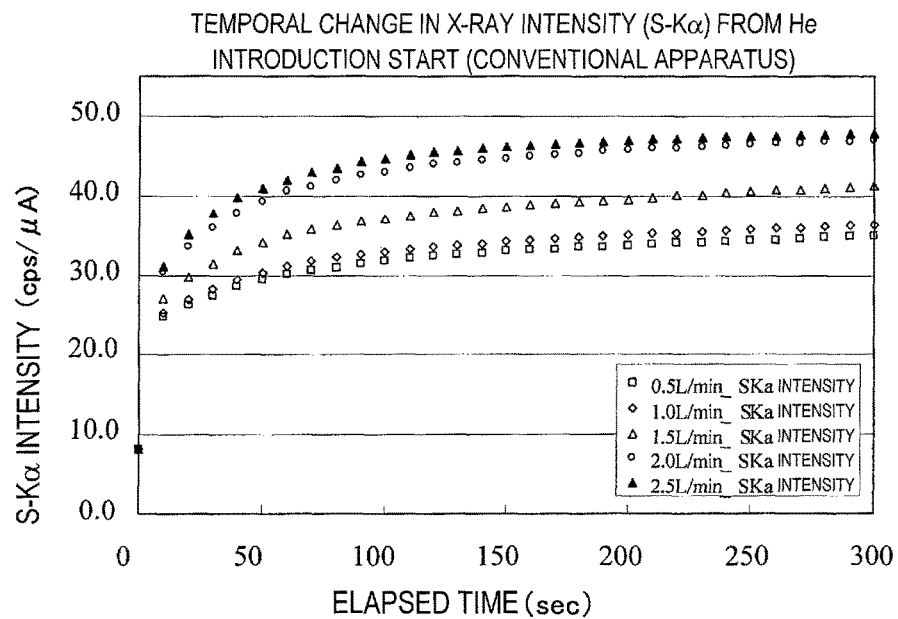
FIG. 4A is a diagram illustrating a temporal change in fluorescent X-ray (S—Kα) intensity of the conventional X-ray fluorescence spectrometer.
Figure 4B:
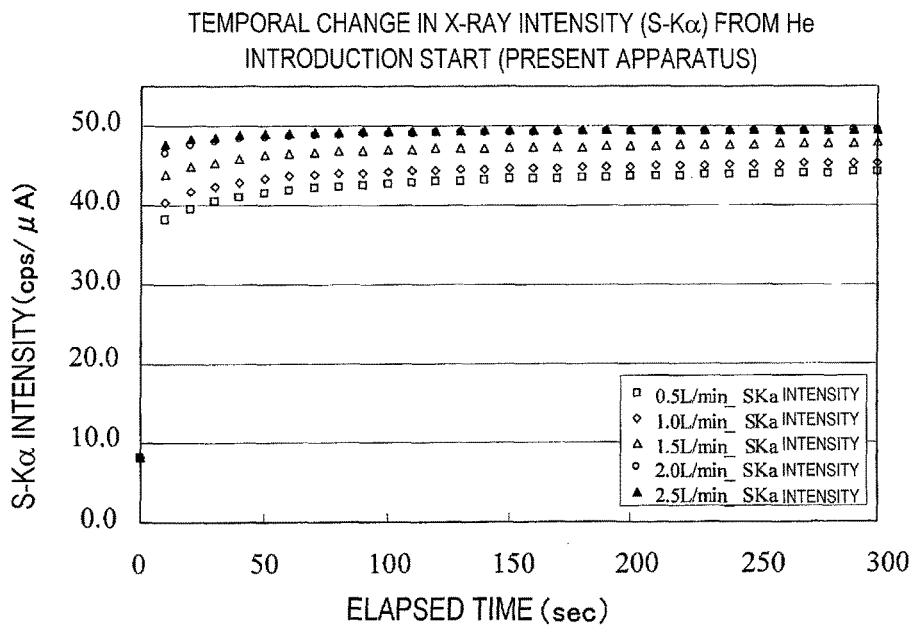
FIG. 4B is a diagram illustrating a temporal change in fluorescent X-ray (S—Kα) intensity of the X-ray fluorescence spectrometer according to the present embodiment.
Figure 5:
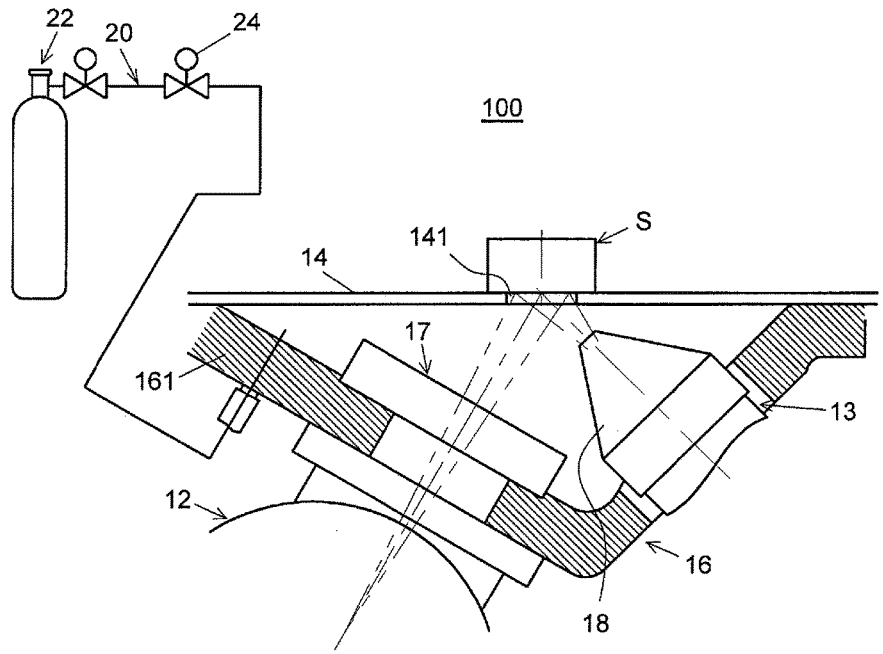
FIG. 5 is a schematic configuration diagram of the conventional X-ray fluorescence spectrometer.

FIG. 2A and FIG. 2B each illustrate a relation between the helium gas flow rate and the He replacement rate. Moreover, FIG. 3A and FIG. 3B each illustrate a change in Na—Kα intensity from a helium gas introduction start, and FIG. 4A and FIG. 4B each illustrate a change in S—Kα intensity from the helium gas introduction start. FIG. 2A, FIG. 3A, and FIG. 4A illustrate results obtained by a conventional X-ray fluorescence spectrometer 100 (see FIG. 5; hereinafter, referred to as a conventional apparatus), and FIG. 2B, FIG. 3B, and FIG. 4B illustrate results obtained by the X-ray fluorescence spectrometer 10 of the present embodiment (hereinafter, referred to as a present apparatus), when helium gas is introduced from the gas introduction port provided to the lower wall 161 of the analysis chamber 16. Moreover, in FIG. 2A and FIG. 2B, the horizontal axis represents the He flow rate (L/min), and the vertical axis represents the He replacement rate (%). It is assumed in FIG. 2A and FIG. 2B that the Na—Kα intensity and the S—Kα intensity when the inside of the analysis chamber 16 is in a vacuum state are each represented by 100%. Moreover, in FIG. 2A and FIG. 2B, the He replacement rate on the detector 13 side (between the sample and the detector) is represented by *, and the He replacement rate on the primary side (between the X-ray tube and the sample) is represented by ♦.

As is apparent from FIG. 2A and FIG. 2B, in the conventional apparatus, the He replacement rate on the primary side was lower than that on the detector 13 side at every He flow rate, and, particularly, the He replacement rate on the primary side was extremely low at a He flow rate of 0.5 to 1.5 L/min. In comparison, in the present apparatus, the He replacement rate on the primary side was slightly lower than that on the detector 13 side at a He flow rate of 0.5 to 1.5 L/min, but was considerably improved. Moreover, the He replacement rates on the detector 13 side and on the primary side were substantially the same as each other at the He flow rates of 1.5 L/min or more, and were equal to or more than 90%.

Moreover, as is apparent from FIG. 3A, FIG. 3B, FIG. 4A, and FIG. 4B, the fluorescent X-ray intensities of Na—Kα and S—Kα of the present apparatus were higher than those of the conventional apparatus immediately after the He introduction start, at every He flow rate. Further, in the conventional apparatus, the fluorescent X-ray intensities of Na—Kα and S—Kα did not reach an equilibrium (stable) state even after the elapse of 300 seconds from the He introduction start. In comparison, in the present apparatus, the fluorescent X-ray intensities of Na—Kα and S—Kα reached an equilibrium state after the elapse of about 100 seconds from the He introduction start, at the He flow rates of 1.5 L/min or more. Accordingly, it is understood that the present apparatus can reduce the time required for the He replacement work, compared with the conventional apparatus.

The following is understood from the above. In the present embodiment, the first gas introduction port 162 is provided near the introduction port 17 for the primary X-ray, the second gas introduction port 164 is provided to the housing 18 for the detector 13, and He is introduced into the analysis chamber 16 through this introduction port 17 and the detection port 181 for this detector 13. Helium gas replacement is difficult for the introduction port 17 for the primary X-ray and the detection port 181 for the detector 13 due to their structures, and the He replacement rates of these portions are low in conventional cases. On the other hand, in the present embodiment, the He replacement rates of the introduction port 17 and the detection port 181 for the detector 13 can be enhanced. As a result, the fluorescent X-ray intensity of each light element detected by the detector 13 increases, and hence the detection sensitivity and the analysis precision can be enhanced. Moreover, because efficient helium gas replacement is possible for the introduction port 17 and the detection port 181 for the detector 13, the time until the fluorescent X-ray intensity becomes stable (reaches an equilibrium state) after helium gas is introduced can be reduced, and the analysis time can be reduced. As a result, the amount of sample analysis per unit time can be increased, and the sample measurement capability can be enhanced.

Second Embodiment

Figure 6:
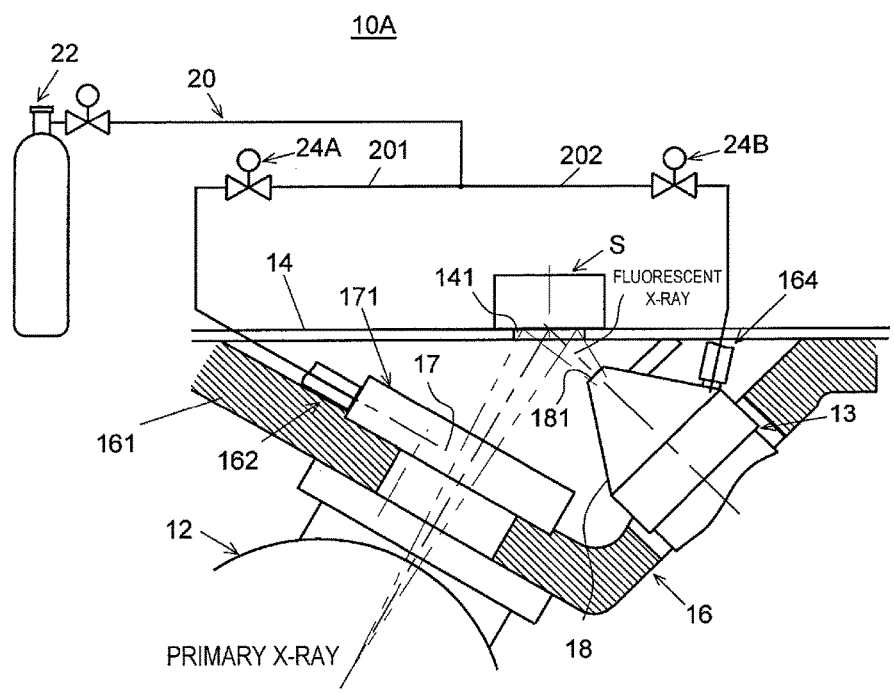
FIG. 6 is a schematic configuration diagram of an X-ray fluorescence spectrometer according to a second embodiment of the present invention.

FIG. 6 illustrates an X-ray fluorescence spectrometer 10A according to a second embodiment of the present invention. In the X-ray fluorescence spectrometer 10A, flow rate control valves 24A and 24B are set to the branch pipes 201 and 202 of the introduction pipe 20, respectively instead of the flow rate control valve 24. The degrees of opening of the flow rate control valves 24A and 24B are individually adjusted by instructions from the control apparatus 25. According to such a configuration, in the present embodiment, the amount of helium gas passing through the branch pipe 201 and the branch pipe 202 can be individually adjusted. Hence, for example, in the case where the introduction port 17 has a more complicated structure than that of the detection port 181 and helium gas less easily flows into the analysis chamber 16 from the introduction port 17, the helium gas flow rate in the branch pipe 201 is set to be higher than that in the branch pipe 202, whereby the amount of helium gas that is introduced into the analysis chamber 16 from the introduction port 17 can be made equal to the amount of helium gas that is introduced into the analysis chamber 16 from the detection port 181.

Third Embodiment

Figure 7:
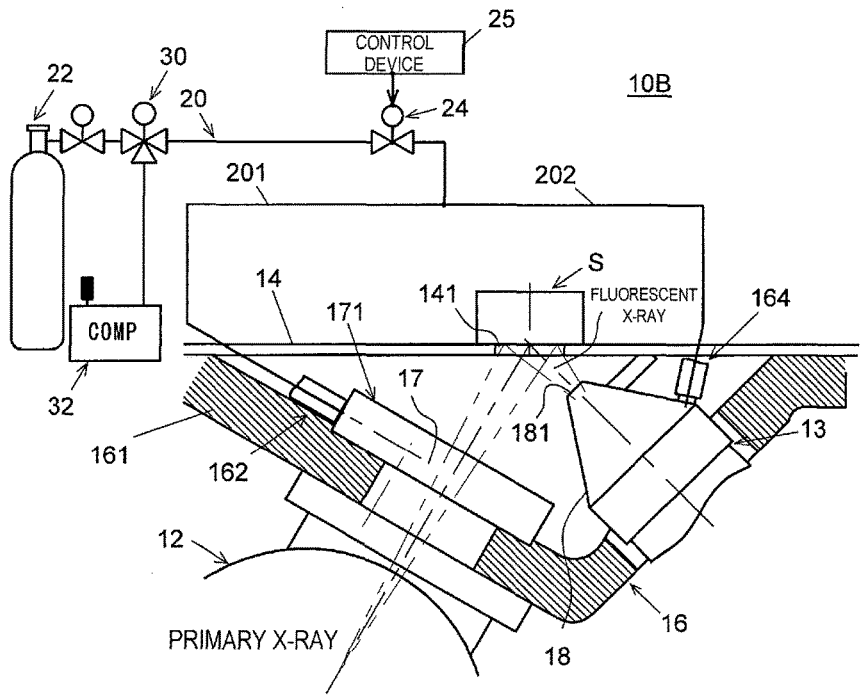
FIG. 7 is a schematic configuration diagram of an X-ray fluorescence spectrometer according to a third embodiment of the present invention.

FIG. 7 illustrates an X-ray fluorescence spectrometer 10B according to a third embodiment of the present invention. The X-ray fluorescence spectrometer 10B is different from the X-ray fluorescence spectrometer 10 of the first embodiment in that: a switching control valve 30 is set to the introduction pipe 20 between the helium gas cylinder 22 and the flow rate control valve 24; and a compressor 32 is connected to the switching control valve 30. When helium gas is introduced into the analysis chamber 16, the switching control valve 30 is switched to communicate the helium gas cylinder 22 with the introduction pipe 20. When an analysis is performed under the atmospheric air, the switching control valve 30 is switched to communicate the compressor 32 with the introduction pipe 20.

The present embodiment can produce the following functions and effects. That is, in the case where an analysis is performed inside which the analysis chamber 16 is replaced with helium gas, next analysis is then performed under the atmospheric air, the inside of the analysis chamber 16 (optical system) is exposed to the atmosphere, but helium gas remaining in the introduction port 17 and the housing 18 may not be completely discharged, and may remain as residual gas. If the analysis is performed in this state, the fluorescent X-ray intensity of each light element detected by the detector 13 becomes higher than that in the case where the analysis is performed inside which the analysis chamber 16 is completely replaced with the atmospheric air, and a quantitative analysis result of each light element is varied by depending on the residual amount of helium gas. In a quantitative analysis using a fundamental parameter (FP) method, quantitative analysis results of light elements significantly influence those of other heavy elements, and hence the unstable quantitative analysis results of the light elements are not preferable.

To deal with this, in the present embodiment, in the case where an analysis is performed under the atmospheric air, the atmospheric air can be forcibly introduced into the analysis chamber 16 by the compressor 32. Accordingly, helium gas remaining in the introduction port 17 and the housing 18 in the leading end part of the detector 13 can be efficiently replaced with the atmospheric air, and hence the quantitative analysis precision can be enhanced. Moreover, the time required to replace the atmosphere inside the analysis chamber 16 with the atmospheric air can be reduced.

Fourth Embodiment

Figure 8:
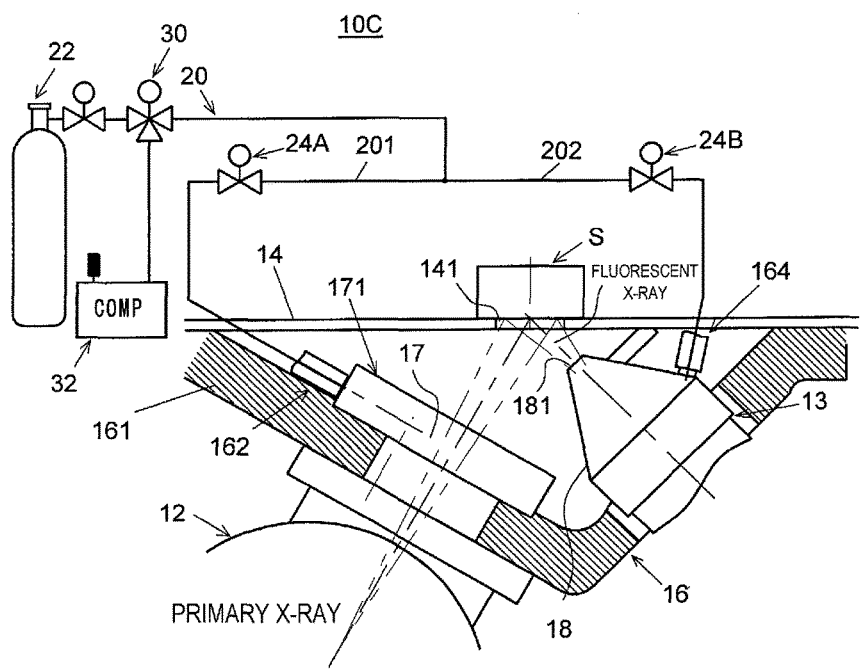
FIG. 8 is a schematic configuration diagram of an X-ray fluorescence spectrometer according to a fourth embodiment of the present invention.

FIG. 8 illustrates an X-ray fluorescence spectrometer 10C according to a fourth embodiment of the present invention. The X-ray fluorescence spectrometer 10C has a configuration in which the switching control valve 30 and the compressor 32 are set to the introduction pipe 20 of the X-ray fluorescence spectrometer 104 (see FIG. 6) of the second embodiment. Such a configuration can also produce functions and effects similar to those produced by the apparatus 10B according to the third embodiment.

The present invention is not limited to the above-mentioned embodiments, and can be variously modified. For example, in all the above-mentioned embodiments, the present invention is applied to a so-called X-ray fluorescence spectrometer of under irradiation type in which the sample placed on the upper surface of the sample stage is irradiated with the primary X-ray from below the sample stage. Alternatively, the present invention can also be applied to: an X-ray fluorescence spectrometer of top irradiation type in which the sample is irradiated with the primary X-ray from above; and an X-ray fluorescence spectrometer of side irradiation type in which the sample is irradiated with the primary X-ray from the side.

REFERENCE SIGNS LIST 10, 10A, 10B, 10C . . . X-ray Fluorescence Spectrometer
12 . . . X-ray Tube
13 . . . Detector
14 . . . Sample Stage
 141 . . . X-ray Passing Port
16 . . . Analysis Chamber
 162 . . . First Introduction Port
 164 . . . Second Introduction Port
18 . . . Housing
 181 . . . Detection Port
20 . . . Introduction Pipe
 201, 202 . . . Branch Pipe
22 . . . Helium Gas Cylinder
24 . . . Flow Rate Control Valve
25 . . . Control Device
30 . . . Control Valve
32 . . . Compressor

The invention claimed is:
1. An X-ray fluorescence spectrometer comprising:
 a) an X-ray source for irradiating a sample with a primary X-ray;
 b) a detector for detecting a fluorescent X-ray that is emitted from the sample when the sample is irradiated with the primary X-ray;
 c) an analysis chamber having an introduction port for the primary X-ray emitted from the X-ray source and a detection port for the detector, the analysis chamber completely confining a space including an optical path of the primary X-ray from the introduction port to the sample and an optical path of the fluorescent X-ray from the sample to the detection port;
 d) first introduction means for introducing helium gas into the analysis chamber through the introduction port;
 e) second introduction means for introducing helium gas into the analysis chamber through the detection port; and
 f) flow rate control means for controlling a flow rate of the helium gas that is introduced into the analysis chamber by each of the first introduction means and the second introduction means.

2. The X-ray fluorescence spectrometer according to claim 1, wherein the flow rate control means includes: first flow rate control means for controlling the flow rate of the helium gas that is introduced into the analysis chamber by the first introduction means; and second flow rate control means for controlling the flow rate of the helium gas that is introduced into the analysis chamber by the second introduction means.

3. The X-ray fluorescence spectrometer according to claim 1, wherein
the first introduction means includes a first introduction pipe having an inlet-side end part connected to a helium gas supply source and an outlet-side end part connected to the introduction port,
the second introduction means includes a second introduction pipe having an inlet-side end part connected to the helium gas supply source and an outlet-side end part connected to the detection port, and
the X-ray fluorescence spectrometer further comprises atmospheric air introduction means for forcibly introducing an atmospheric air into the analysis chamber from at least one of the first introduction pipe and the second introduction pipe.

4. The X-ray fluorescence spectrometer according to claim 2, wherein
the first introduction means includes a first introduction pipe having an inlet-side end part connected to a helium gas supply source and an outlet-side end part connected to the introduction port,
the second introduction means includes a second introduction pipe having an inlet-side end part connected to the helium gas supply source and an outlet-side end part connected to the detection port, and
the X-ray fluorescence spectrometer further comprises atmospheric air introduction means for forcibly introducing an atmospheric air into the analysis chamber from at least one of the first introduction pipe and the second introduction pipe.

* * * * *